(12) United States Patent
Bot et al.

(10) Patent No.: US 7,141,236 B2
(45) Date of Patent: Nov. 28, 2006

(54) METHODS AND COMPOSITIONS FOR DELIVERING MACROMOLECULES TO OR VIA THE RESPIRATORY TRACT

(75) Inventors: Adrian I. Bot, San Diego, CA (US); Luis A. Dellamary, San Marcos, CA (US); Dan J. Smith, San Diego, CA (US)

(73) Assignee: Nektar Therapeutics, San Carlos, CA (US)

( * ) Notice: Subject to any disclaimer, the term of this patent is extended or adjusted under 35 U.S.C. 154(b) by 616 days.

(21) Appl. No.: 10/132,215

(22) Filed: Apr. 26, 2002

(65) Prior Publication Data

US 2003/0007930 A1   Jan. 9, 2003

Related U.S. Application Data

(63) Continuation-in-part of application No. 09/919,477, filed on Jul. 30, 2001, now abandoned.

(60) Provisional application No. 60/286,891, filed on Apr. 26, 2001, provisional application No. 60/221,544, filed on Jul. 28, 2000.

(51) Int. Cl.
*A61K 9/00* (2006.01)
*A61K 9/12* (2006.01)
*A61K 9/127* (2006.01)
*A61K 9/14* (2006.01)

(52) U.S. Cl. .................. 424/45; 424/450; 424/491; 424/493

(58) Field of Classification Search ............... 424/45, 424/46, 450, 488, 491, 493
See application file for complete search history.

(56) References Cited

U.S. PATENT DOCUMENTS

| | | | |
|---|---|---|---|
| 5,043,158 A | 8/1991 | Sleytr et al. | |
| 5,308,620 A | 5/1994 | Yen | |
| 5,616,311 A | 4/1997 | Yen | |
| 5,759,572 A | * 6/1998 | Sugimoto et al. | ........... 424/450 |
| 5,807,552 A | 9/1998 | Stanton et al. | |
| 5,855,913 A | 1/1999 | Hanes et al. | |
| 5,985,309 A | 11/1999 | Edwards et al. | |
| 6,071,497 A | 6/2000 | Steiner et al. | |

FOREIGN PATENT DOCUMENTS

| | | |
|---|---|---|
| EP | 0 274 431 B1 | 7/1988 |
| EP | 0 372 777 B1 | 6/1990 |
| EP | 0 611 567 A1 | 8/1994 |
| WO | 88 01862 | 3/1988 |
| WO | 99/16419 | 4/1999 |
| WO | 99/16420 | 4/1999 |
| WO | 99/16421 | 4/1999 |
| WO | 99/16422 | 4/1999 |
| WO | 00/00215 | 1/2000 |
| WO | 01/13891 A2 | 3/2001 |
| WO | 01/85136 A2 | 11/2001 |
| WO | 01/85137 A2 | 11/2001 |

OTHER PUBLICATIONS

Johnson, Preparation of peptide and protein powders for inhalation, Advanced Drug Delivery Reviews 26 (1997) 3-15*
Mitra et al, Enhanced Pulmonary Delivery of Insulin by Lung Fluid and Phospholipids, International Journal of Pharmaceutics 217 (2001) 25-31.*
International Search Report, PCT/US02/13145, issued Aug. 20, 2002.

* cited by examiner

*Primary Examiner*—Johann Richter
*Assistant Examiner*—Mina Haghighatian
(74) *Attorney, Agent, or Firm*—Ashok K. Janah; Guy Tucker

(57) ABSTRACT

Methods and compositions for delivering macromolecules to or via the respiratory tract, such that the macromolecules exhibit improved local and/or systemic bioavailability are provided. Such methods utilize lipid-based microstructures formed in combination with at least one bioactive macromolecule, which have a superior ability to rapidly release the bioactive macromolecule(s) thereby resulting in improved local and/or systemic bioavailability of the bioactive macromolecule(s). Such improved bioavailability is believed to be due, in part, to reduction of scavenging by bronchoalveolar macrophages and/or mucociliary clearance. Compositions with improved bioavailability are provided comprising a plurality of lipid-based microstructures formed in combination with at least one bioactive macromolecule, wherein the bioavailability of the bioactive macromolecule is improved by modifying the rate of release of the bioactive macromolecule from the microstructure thereby reducing scavenging by bronchoalveolar macrophages and/or mucociliary clearance.

39 Claims, 6 Drawing Sheets

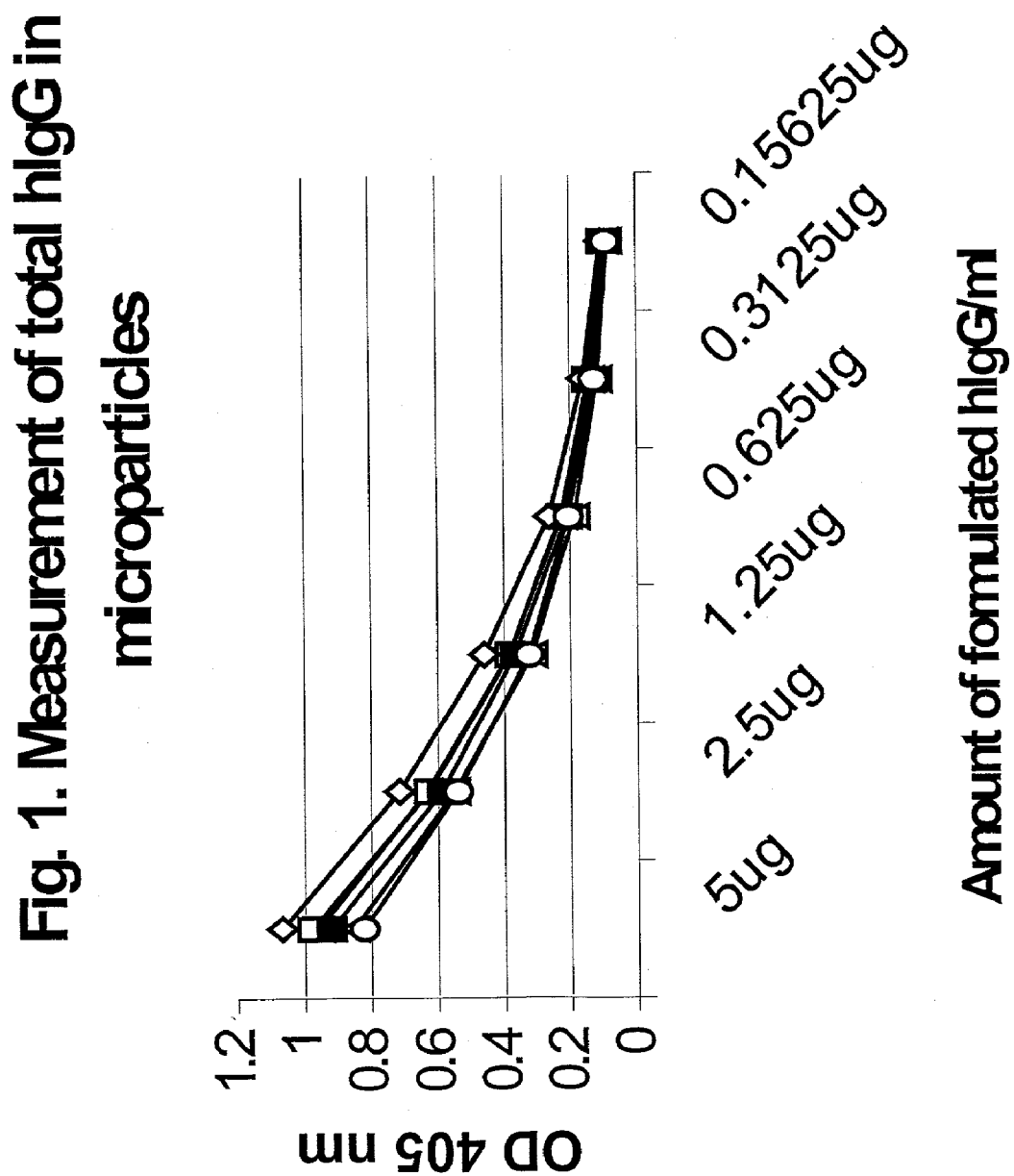

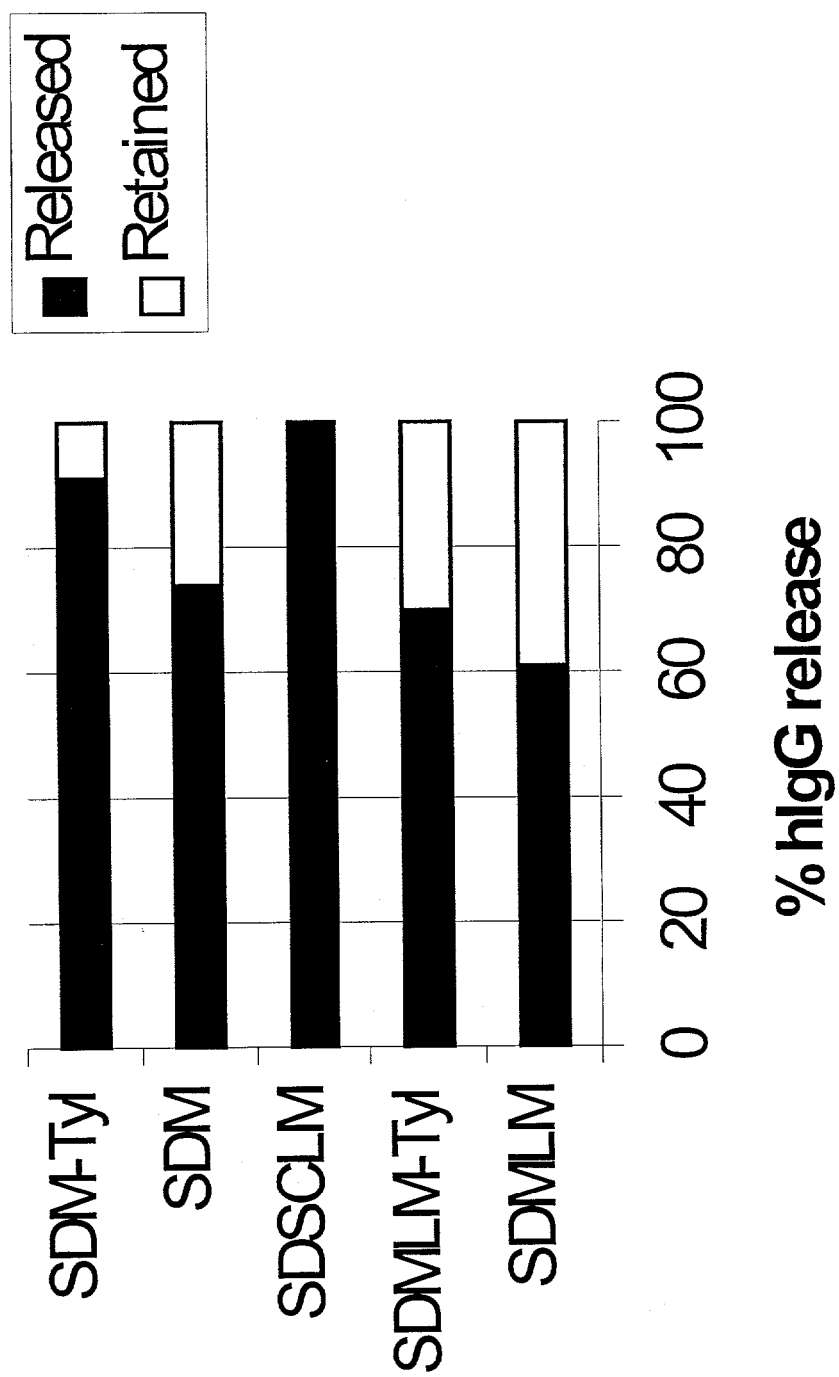

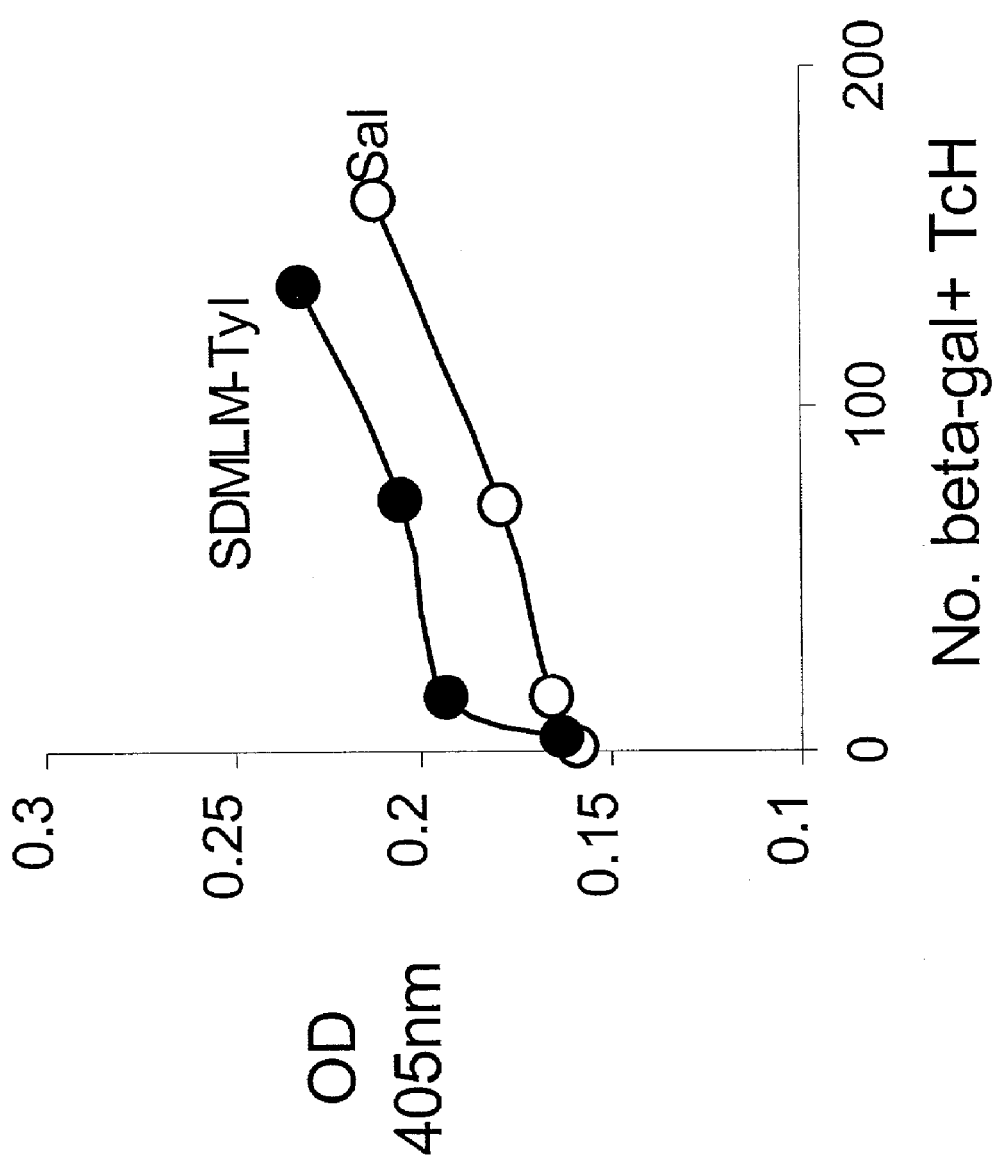
Fig. 3. Bioactivity of formulated anti-CD3$_\varepsilon$ mAb

Fig. 4A. Pulmonary delivery of hIgG

Fig. 4B. Lung delivery of hIgG by microparticles (1 hour)

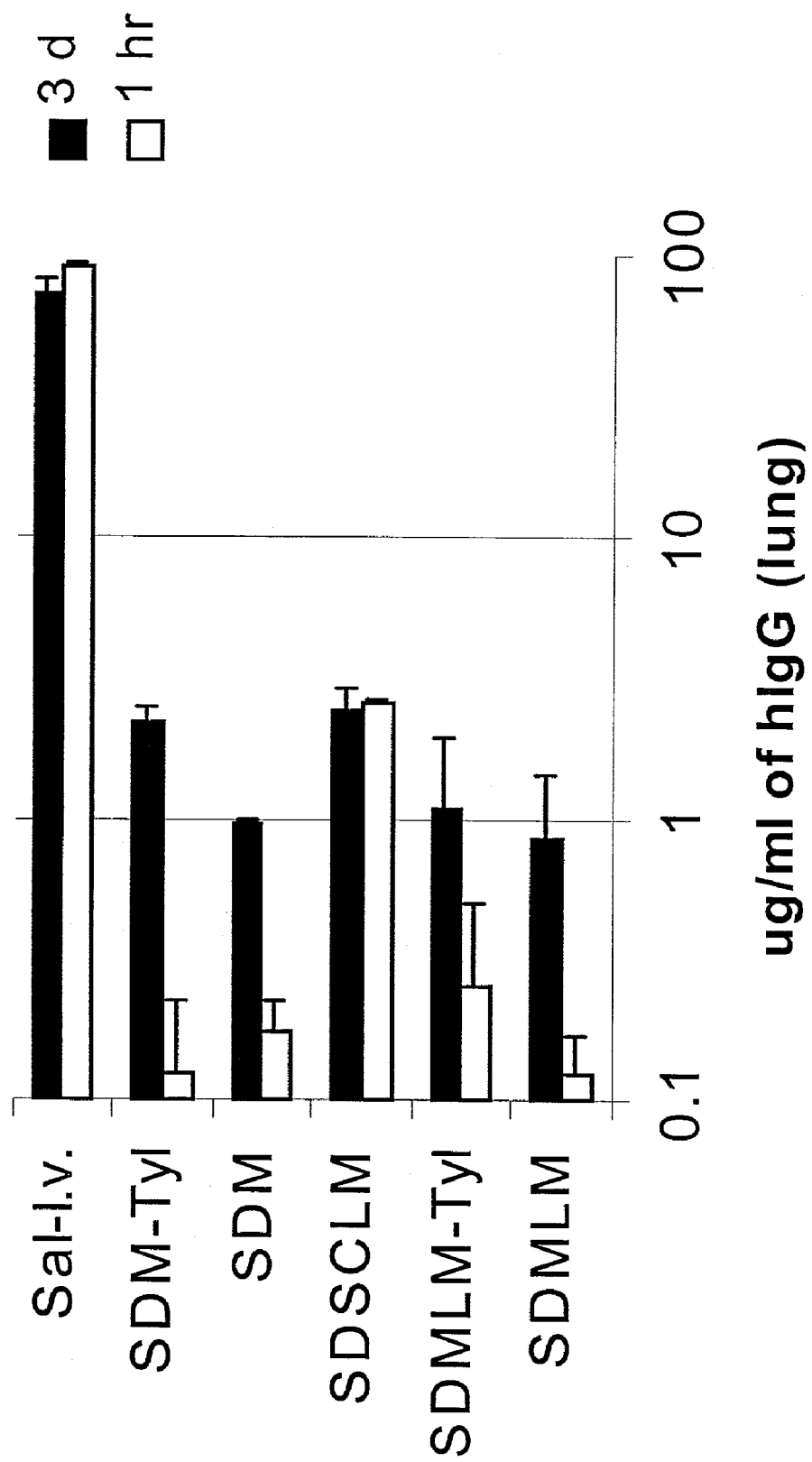
Fig. 5. Systemic delivery of hIgG via lung

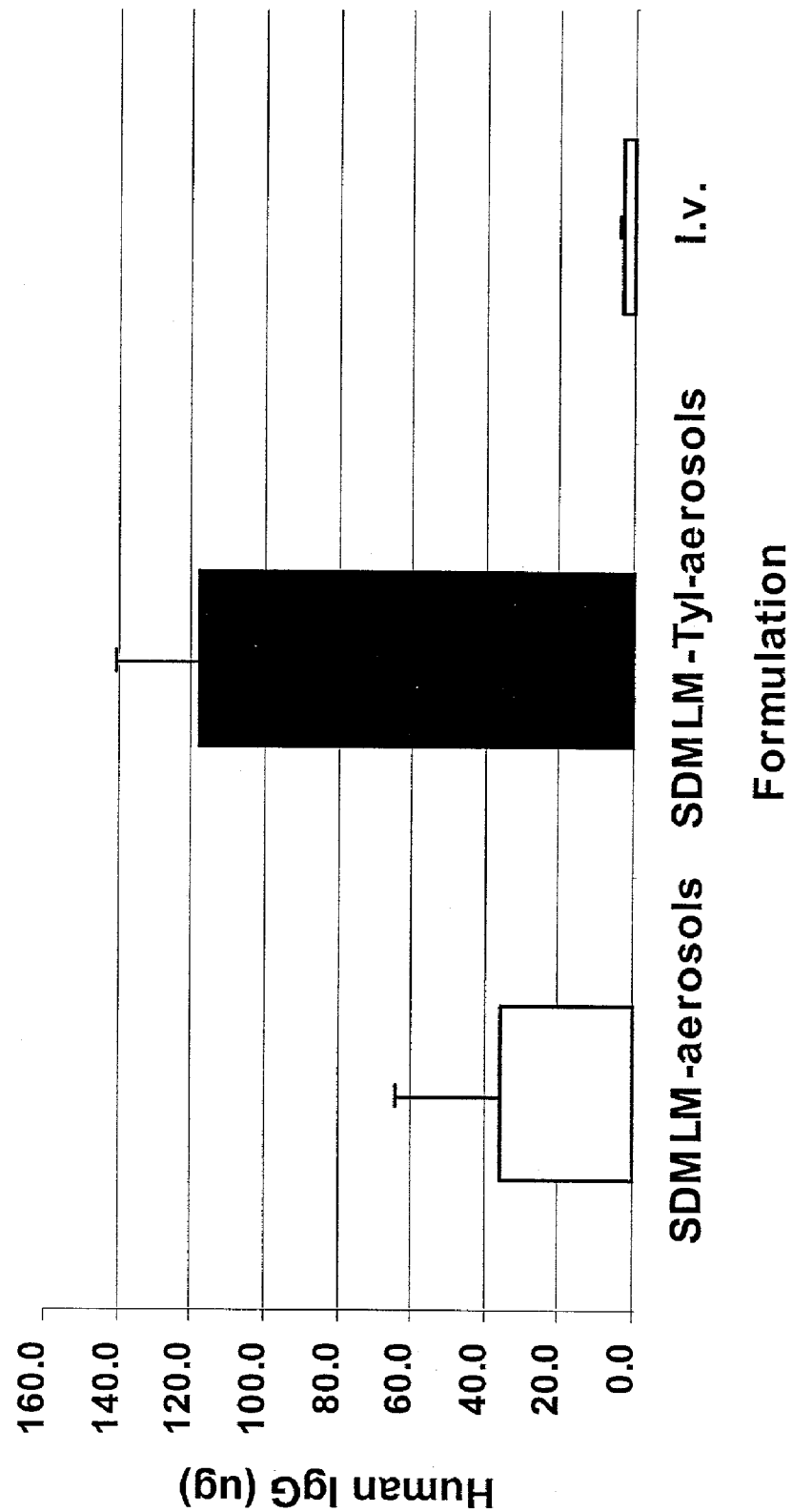

METHODS AND COMPOSITIONS FOR DELIVERING MACROMOLECULES TO OR VIA THE RESPIRATORY TRACT

RELATED APPLICATIONS

The present application claims the benefit of U.S. Provisional Patent Application Ser. No. 60/286,891 filed Apr. 26, 2001, and is a continuation-in-part of co-pending U.S. patent application Ser. No. 09/919,477 filed on Jul. 30, 2001, which claims the benefit of U.S. Provisional Patent Application Ser. No. 60/221,544 filed Jul. 28, 2000, the disclosures of which are all hereby incorporated by reference in their entirety.

FIELD OF THE INVENTION

The present invention relates generally to the field of drug delivery. More particularly, the present invention relates to novel methods and compositions for drug delivery of bioactive macromolecules with improved bioavailability to or via the respiratory tract.

BACKGROUND OF THE INVENTION

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung (Critical Reviews in Therapeutic Drug Carrier Systems, 6: 273–313 (1990)).

Delivery of bioactive macromolecules to or via the respiratory tract may be useful for the purposes of prophylaxis and therapy of diseases and disorders of the respiratory tract or pulmonary system. For example, local diseases of the pulmonary system may be associated with local antigens such as microbial antigens (respiratory syncytial virus, influenza virus, Streptococcus), tumor antigens (melanoma associated antigens, Neu-2), and inflammation-associated antigens (CD4, IgE). Further, systemic delivery of bioactive macromolecules via the respiratory tract may be useful for prophylaxis or treatment of certain disorders that affect organs other than the lungs. Such systemic diseases may, for example, be associated with tumor antigens (CD20, CEA) or inflammation related antigens (TNFα).

Drug delivery to or via the respiratory tract is an attractive alternative to oral, transdermal, and parenteral administration because self-administration is simple, the lungs provide a large mucosal surface for drug absorption, there is no first-pass liver effect of absorbed drugs, and there is reduced enzymatic activity and pH mediated drug degradation compared with the oral route. Limited bioavailability of many molecules, including macromolecules, can be achieved via inhalation. As a result, several aerosol formulations of therapeutic drugs are in use or are being tested for delivery to the lung (J. Controlled Release, 28: 79–85 (1994); Pharm. Res., 12(9): 1343–1349 (1995); and Pharm. Res., 13(1): 80–83 (1996)).

Drugs currently administered by inhalation come primarily as liquid aerosol formulations. However, many drugs and excipients, especially macromolecules such as proteins and peptides, are unstable in aqueous environments for extended periods of time (Biotechnol. Bioeng., 37: 177–184 (1991)). This can make storage as a liquid formulation problematic. In addition, protein denaturation can occur during aerosolization with liquid formulations (Pharm. Res., 11: 12–20 (1994)). Considering these and other limitations, dry powder formulations (DPF's) are gaining increased interest as formulations for respiratory delivery (EP 0 611 567 A1). However, among the disadvantages of conventional DPF's is that powders of ultrafine particulates usually have poor flowability and aerosolization properties, leading to relatively low respirable fractions of aerosol, i.e., the fractions of inhaled aerosol that escape deposition in the mouth and throat. Another concern with many aerosols is particulate aggregation caused by particle-particle interactions, such as hydrophobic, electrostatic, and capillary interactions. An effective dry-powder inhalation therapy for both short and long term release of macromolecules, either for local or systemic delivery, requires a powder that displays minimum aggregation, as well as a means of avoiding or suspending the lung's natural clearance mechanisms until drugs have been effectively delivered. However, mere engineering of aerosols for optimal aerodynamic and stability characteristics may not necessarily result in desired drug release profiles.

The human lungs can remove or rapidly degrade hydrolytically cleavable deposited particles over periods ranging from minutes to hours. In the upper airways, ciliated epithelia contribute to "mucociliary clearance," by which particles are swept from the airways toward the mouth. In the deep lungs, alveolar macrophages are capable of phagocytosing particles soon after their deposition. In fact, some references clearly show that a substantial fraction of macromolecule-loaded particles are scavenged by airway macrophages within 10–60 minutes upon delivery to the respiratory tract (Pharma. Res., 17: 275 (2000)). As the diameter of particles exceeds 3 µm, there is increasingly less phagocytosis by macrophages. However, increasing the particle size also has been found to minimize the probability of particles (possessing standard mass density) entering the airways and penetrating the alveoli due to excessive deposition in the oropharyngeal or nasal regions (J. Aerosol Sci., 17: 811–825 (1986)). These particles that do not penetrate into alveoli are then cleared by the mucociliary system within 10–30 minutes after delivery.

In sum, conventional respiratory tract drug delivery strategies present many difficulties for the delivery of macromolecules, including macromolecule denaturation, excessive loss of inhaled drug in the oropharyngeal cavity through mucociliary clearance, and phagocytosis by lung macrophages. In addition, in contrast to small hydrosoluble drugs, macromolecules have a tendency to interact with certain excipients, resulting in retentive structure that thereby limits bioavailability. Thus, there remains a need for improved respiratory tract drug delivery strategies for delivering macromolecules. More particularly, there is a need for the development of methods and compositions which are capable of delivering bioactive macromolecules in an effective amount into the airways or the alveolar zone of the lung for local and/or systemic delivery of the bioactive macromolecule.

It is therefore an object of the present invention to provide improved methods and compositions for the delivery of macromolecules to or via the respiratory tract. It is a further object of the invention to provide inhaled pharmaceutical formulations which effectively deliver macromolecules to the deep lung. It is another object of the invention to provide methods and compositions for delivering macromolecules to or via the respiratory tract such that the macromolecules exhibit improved local and/or systemic bioavailability. It is yet another object of the invention to provide methods and compositions for delivering macromolecules to or via the respiratory tract such that mucociliary clearance and/or macrophage scavenging are reduced.

SUMMARY OF THE INVENTION

The present invention generally relates to novel methods and compositions for delivering macromolecules to or via the respiratory tract, such that the macromolecules exhibit improved local and/or systemic bioavailability.

To this end, one aspect of the present invention relates to lipid-based microstructures formed in combination with at least one bioactive macromolecule, which have a superior ability to rapidly release the bioactive macromolecule(s) thereby resulting in improved local and/or systemic bioavailability of the bioactive macromolecule(s). Such improved bioavailability is believed to be due, in part, to reduction of scavenging by bronchoalveolar macrophages and/or mucociliary clearance.

More particularly, in one aspect of the invention, novel compositions with improved bioavailability are provided comprising a plurality of lipid-based microstructures formed in combination with at least one macromolecule, wherein the bioavailability of the macromolecule is improved by modifying the rate of release of the macromolecule from the microstructure thereby reducing scavenging by bronchoalveolar macrophages and/or mucociliary clearance.

In a preferred embodiment, the novel microstructure compositions are formulated to be compatible with drug delivery to or via the respiratory tract through, e.g., nasal or inhaled administration.

BRIEF DESCRIPTION OF THE DRAWINGS

FIG. 1 shows measurement of the amount of immunoglobulin formulated in various microstructures of the present invention;

FIG. 2 shows the percentage of immunoglobulin released from various microstructures of the present invention within a 15 minute interval in an aqueous environment, FIG. 3 shows that the functional structure of a prototype monoclonal antibody endowed with biological activity is retained upon formulation;

FIG. 4A demonstrates enhanced local delivery of immunoglobulins to the pulmonary tissue via the respiratory administration route compared to intravenous administration;

FIG. 4B demonstrates enhanced local delivery of immunoglobulins to the pulmonary tissue via respiratory administration of the microstructures of the present invention;

FIG. 5 demonstrates enhanced systemic delivery of immunoglobulins via respiratory administration of the microstructures of the present invention; and, FIG. 6 demonstrates enhanced bioavailability of detergent co-formulated microstructures of the present invention subsequent to aerosolization into the airways.

DETAILED DESCRIPTION

In one aspect, the present invention teaches the design of novel pharmaceutical formulations for delivery to or via the respiratory tract comprising a plurality of lipid-based microstructures that quickly release incorporated macromolecules, thereby reducing macrophage scavenging and mucociliary clearance to improve bioavailability of the macromolecules. Particularly, quick release of the incorporated macromolecules can at least partially avoid scavenging by Fc-gamma receptor-expressing bronchoalveolar macrophages. The novel compositions disclosed herein may be used to effectively deliver macromolecules to tissues of the respiratory tract, or systemically to the blood subsequent to respiratory administration.

The compositions of the present invention have an improved ability over conventional particle-based formulations to rapidly release the incorporated macromolecule payload, thereby reducing microstructure and/or bioactive macromolecule scavenging and clearance to result in improved bioavailability of the macromolecule. The improved bioavailability is associated with a near-complete release of the macromolecules within 30 minutes after administration to the airway or exposure to an aqueous environment. In a preferred embodiment, the disclosed compositions can be used to modulate the release rate of the incorporated macromolecules from the lipid-based microstructures.

In this regard, it was unexpectedly discovered that the local and/or systemic bioavailability of macromolecules is dependent on the release profile of the macromolecules upon administration, and that the release profile can be tightly controlled. More particularly, it was unexpectedly discovered according to the present invention that the rate of release of incorporated macromolecules from lipid-based microstructures can be achieved by (a) modifying the type and amount of the major lipid excipient and/or carbohydrate co-excipients, (b) the addition of co-excipients with surfactant-detergent properties, and/or (c) modulation of the ionic content of the final formulation.

A. Compositions

The compositions of the present invention are comprised of a plurality of lipid-based microstructures that comprise a major lipid excipient and at least one macromolecule. The lipid-based microstructures of the invention can further comprise minor co-excipients such as carbohydrates, polyvalent metal ions, detergent surfactants, and combinations thereof. The macromolecule can be any therapeutic or prophylactic macromolecule known in the art such as peptides, proteins, nucleotides, antibodies, immunoglobulins, etc.

1. Microstructure Components

The major lipid excipient may be present in the microstructure in an amount ranging from about 10% to about 89% by weight, preferably about 25% to about 75% by weight, and most preferably about 50% by weight, based on the total weight of the microstructure. The macromolecule may be included in a range of about 5% to about 89% by weight, preferably about 15% to about 65% by weight, and more preferably about 25% by weight, based on the total weight of the microstructure. Carbohydrate co-excipients may be present in the microstructure an amount 70% by weight or less, preferably between about 5% and about 50% by weight, and most preferably about 10% by weight, based on the total weight of the microstructure. Biocompatible polyvalent metal ion co-excipients may be present in the microstructure in a metal/lipid molar ratio of about 2 or less, preferably a molar ratio of about 1. Detergent surfactant co-excipients may be included in the microstructure in an amount of about 10% by weight or less, preferably about 0.5% to about 5% by weight, and more preferably about 1% by weight, based on the total weight of the microstructure.

Preferred major lipid excipients include phosphatides such as homo and heterochain phosphatidylcholines (PC's), phosphatidylserines (PS's), phosphatidylethanolamines (PE's), phosphatidyiglycerols (PG's), phosphatidylinositols (PI's), sphingomyelins, gangliosides, 3-trimethylammonium-propane phosphatides (TAP's) and dimethylammonium-propane phosphatides (DAP's), having hydrocarbon chain length ranging from 5 to 22 carbon atoms. Single (lysophosphatides) or double chain phosphatides are also contemplated. The phosphatides may be hydrogenated, unsaturated or partially hydrogenated. Preferred phosphatides are natural phosphatides and hydrogenated phosphatides derived from soy or egg, partially hydrogenated phosphatides derived from soy and egg, dipalmitoleioylphosphatidylcholine (DiC18PC), distearoylnhosphatidylcholine (DiC16PC), dipalmitoylphosphatidylcholine (DiC14PC), dicaproylphosphatidylcholine (DiC8PC), dioctanoylphosphatidylcholine (DiC6PC), distearoylphosphatidylserine (DiC16PS), dipalmitoylphosphatidylserine (DiC14PS), dicaproylphosphatidylserine (DiC8PS) and dioctanoylphosphatidylserine (DiC6PS). As used herein, short-chain phosphatides include those having a hydrocarbon chain length ranging from 5 to 10 carbon atoms. Particularly preferred phosphatides include distearoylphosphatidylcholine (DiC16PC), dipalmitoylphosphatidylcholine (DiC14PC), and dioctanoylphosphatidylcholine (DiC6PC).

Preferred carbohydrate co-excipients for use in the lipid-based microstructures disclosed herein include monosaccharides, disaccharides and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as hetastarch, starches (hydroxyethylstarch), dextrins, cyclodextrins and maltodextrins, lactose, mannitol, mannose, inulin, mannan, sorbitol, sucrose, trehalose, raffinose, maltose, glucose, cellulose, pectins, saponins, chitosan, chitin, mucopolysaccharides, chondroitin sulfate etc. Other optional co-excipients can include proteins such as albumin (human, egg or bovine), oligopeptides, oligoleucine, oligoalanine, etc.; osmotic agents such as NaCl, KCl, magnesium chloride, calcium chloride, zinc chloride, etc.; and buffer systems such as PBS, acetate, citrate, tris, etc.

Preferred polyvalent metal ions include metal ions or salts from groups IIa, IIIa and metal ions from atomic numbers 21–30; 39–48, 57–80 and 89–106. The preferred polyvalent metal ions are calcium, magnesium, aluminum and zinc. Further, the polyvalent metal ions may be provided in salt form.

Contemplated detergent surfactants may include non-ionic surfactants such as POLOXAMER's (polyethylene-polypropylene glycol, which is a nonionic polyoxyethylene-polyoxypropylene block co-polymer), TWEEN's (polyoxyethylene sorbitan monolaurate), TRITON 's (2,4,6-Trinitrotoluene), PEG's (polyethylene gycols), and sugar esters. Most preferable detergent surfactants are POLOXAMER 188 (polyethylene-polypropylene glycol with an average molecular weight of 8400 g/mol), POLOXAMER 407 (polyethylene-polypropylene glycol with an average molecular weight of 12,500 g/mol), TWEEN 80 (polyoxyethylene sorbitan monooleate), PEG 1540 (polyethylene gycols with an average molecular weight of 1500 g/mol). cetyl alcohol, and TYLOXAPOL (phenol, 4-(1,1,3,3-tetramethyibutyl) polymer with formaldehyde and oxirane). Cationic-surfactants may include benzalkonium chloride. Anionic surfactants may be selected from the cholate and deoxycholate family, such as CHAPS (sulfobetaine-type zwitterionic detergent) (MERCK index 11 ed., monography pg. 2034), taurocholate, deoxytaurocholate, or phosphate fatty acid salts such as dicetyl phosphate. Other surface active compounds include albumin, leucine, oligopeptides, oligoleucine, oligoalanine and saponins (for a further listing see Cowers handbook of industrial surfactants 1993, pages 885–904, ISBN 0566074575 which is hereby incorporated by reference).

Any of a variety of therapeutic or prophylactic macromolecules can be incorporated within the lipid-based microstructures of the invention. The microstructures of the invention can thus be used to locally or systemically deliver a variety of therapeutic or prophylactic agents to an animal. Examples of contemplated macromolecules include proteins, peptides, immunogenic agents, polysaccharides, other sugars, lipids, and nucleic acid sequences having therapeutic or prophylactic activities. Immunogenic agents can include, but are not limited to, protein antigens or antigenic fragment, antibodies or single-chain binding molecules, and immunoglobulins or immunoglobulin-like molecules. Nucleic acid sequences can include genes, antisense molecules which bind to complementary DNA to inhibit transcription, and ribozymes.

The macromolecules to be incorporated can have a variety of biological activities, such as vasoactive agents, neuroactive agents, hormones, anticoagulants, immunomodulating agents, cytotoxic agents, prophylactic agents, antibiotics, antivirals, antisense, antigens, and antibodies. In some instances, the proteins may be immuno active agents such as antibodies, immunoglobulins, or antigens which otherwise would have to be administered by injection to elicit an appropriate response. Compounds with a wide range of molecular weight can be utilized, for example, between 100 and 500,000 grams or more per mole.

In one aspect of the invention, the microstructures described herein may include a macromolecule for local delivery within the lung, such as macromolecules for the treatment of asthma, emphysema, or cystic fibrosis. Alternatively, the microstructures may include a macromolecule for systemic delivery. For example, contemplated bioactive macromolecules include, but are not limited to, insulin, calcitonin, leuprolide (or gonadotropin-releasing hormone ("LHRH")), granulocyte colony-stimulating factor ("G-CSF"), parathyroid hormone-related peptide, somatostatin, testosterone, progesterone, estradiol, norethisterone, clonidine, scopolomine, salicylate, cromolyn sodium, salmeterol, formeterol, albuterol, and valium.

Besides the aforementioned co-excipients, it may be desirable to add other excipients to the lipid-based microstructures of the present invention to improve particle rigidity, production yield, emitted dose and deposition, shelf-life and patient acceptance. Such optional excipients include, but are not limited to: coloring agents, taste masking agents, buffers, hygroscopic agents, antioxidants, and chemical stabilizers. Further, various excipients may be incorporated in, or added to, the lipid-based microstructure to provide structure and form to the microstructure compositions (i. e. microspheres such as latex particles). In this regard it will be appreciated that the rigidifying components can be removed using a post-production technique such as selective solvent extraction.

2. Microstructure Physical Parameters

It will be appreciated that the lipid-based microstructures disclosed herein can comprise any suitable structural matrix known in the art, such as particulates, microparticulates, perforated microstructures, and combinations thereof. In a particularly preferred embodiment of the invention, the microstructures comprise a structural matrix of spray dried, hollow and porous particulates, as disclosed in WO 99/16419, which is hereby incorporated by reference in its entirety. Such hollow and porous particulates comprise particles having a relatively thin porous wall defining a large internal void, although, other void containing or perforated structures are contemplated as well. The absolute shape (as opposed to the morphology) of the perforated microstructure is generally not critical and any overall configuration that provides the desired characteristics is contemplated as being within the scope of the invention. Accordingly, preferred embodiments can comprise approximately microspherical shapes. However, collapsed, deformed or fractured particulates are also compatible.

The lipid-based microstructures of the present invention preferably have a mean aerodynamic diameter less than about 10 µm, more preferably ranging from about 0.5 µm to about 5 µm. "Aerodynamic diameter," as used herein, is a measure of the aerodynamic size of a dispersed microstructure. The aerodynamic diameter is used to describe an aerosolized microparticles in terms of its settling behavior, and is the diameter of a unit density sphere having the same settling velocity, generally in air, as the microstructure. The aerodynamic diameter encompasses microstructure shape, density, and physical size.

The lipid-based microstructures of the present invention preferably have a mean geometric diameter ranging from about 1 µm to about 30 µm, preferably from about 1 µm to about 10 µm. A particularly preferred embodiment is directed to microstructures having a mean geometric diameter of about 1 µm to about 5 µm. Because the compositions of the present invention are generally polydisperse (i.e., consist of a range of microstructure sizes), "mean geometric diameter" is used as a measure of mean microstructure size. Mean geometric diameters as reported herein are determined by laser diffraction, although any number of commonly employed techniques can be used.

The lipid-based microstructures of the present invention typically have bulk densities less than about 0.5 $g/cm^3$, preferably less than about 0.3 $g/cm^3$, more preferably less 0.1 $g/cm^3$, and most preferably less than 0.05 $g/cm^3$. By providing microstructures with low bulk density, the minimum powder mass that can be filled into a unit dose container is reduced, which eliminates the need for carrier particles. That is, the relatively low density of the microstructures of the present invention provides for the reproducible administration of relatively low dose macromolecules. Moreover, the elimination of carrier particles will potentially minimize throat deposition and any "gag" effect from the large carrier particles impacting the throat and upper airways upon administration.

3. Optional Composition Components

The compositions of the present invention can further comprise non-aqueous carriers or suspension media. For instance, the lipid-based microstructures of the present invention may optionally be dispersed in non-aqueous media to thereby be compatible with aerosolization or delivery by instillation in non-aqueous suspension media. By way of example, such non-aqueous suspension media can include hydrofluoroalkanes, fluorocarbons, perfluorocarbons, fluorocarbon/hydrocarbon diblocks, hydrocarbons, alcohols, ethers, and combinations thereof. However, it is understood that any non-aqueous suspension media known in the art may be used in conjunction with the present invention.

B. Administration

In a preferred aspect of the invention, the compositions disclosed herein can be formulated for delivery to or via the respiratory tract of a patient in need of treatment. Such formulations can be delivered to or via the respiratory tract for prophylactic or therapeutic purposes in any manner known in the art such as, but not limited to, dry-powder inhalation, instillation, metered dose inhalation, nebulization, aerosolization, or instillation as suspension in compatible vehicles. Other routes of administration are also contemplated, such as topical, transdermal, intradermal, intraperitoneal, intravenous, intramuscular, subcutaneous, vaginal, rectal, aural, oral, or ocular administration.

As discussed above, the compositions disclosed herein may be administered to the respiratory tract of a patient via aerosolization, such as with a dry powder inhaler (DPI). The use of such microstructures provides for superior dispersibility and improved lung deposition as disclosed in WO 99/16419, hereby incorporated in its entirety by reference. DPIs are well known in the art and could easily be employed for administration of the claimed microsturctures without undue experimentation.

The compositions disclosed herein may also be administered to the respiratory tract of a patient via aerosolization, such as with a metered dose inhaler (MDI). The use of such stabilized preparations provides for superior dose reproducibility and improved lung deposition as disclosed in WO 99/16422, hereby incorporated in its entirety by reference. MDIs are well known in the art and could easily be employed for administration of the claimed dispersions without undue experimentation.

Breath activated MDIs, as well as those comprising other types of improvements which have been, or will be, developed are also compatible with the stabilized dispersions and present invention and, as such, are contemplated as being within the scope thereof.

However, it should be emphasized that, in preferred embodiments, the compositions may be administered with an MDI using a number of different routes including, but not limited to, topical, nasal, pulmonary or oral. Those skilled in the art will appreciate that, such routes are well known and that the dosing and administration procedures may be easily derived for the stabilized dispersions of the present invention.

Along with the aforementioned embodiments, the compositions of the present invention may also be used in conjunction with nebulizers as disclosed in PCT WO 99/16420, the disclosure of which is hereby incorporated in its entirety by reference, in order to provide an aerosolized medicament that may be administered to the pulmonary air passages of a patient in need thereof. Nebulizers are well known in the art and could easily be employed for administration of the claimed dispersions without undue experimentation.

Breath activated nebulizers, as well as those comprising other types of improvements which have been, or will be, developed are also compatible with the stabilized dispersions and present invention and are contemplated as being with in the scope thereof.

Along with DPFs, MDIs and nebulizers, it will be appreciated that the compositions of the present invention may be used in conjunction with liquid dose instillation (LDI) or LDI techniques as disclosed in, for example, WO 99/16421 hereby incorporated by reference in its entirety. Liquid dose instillation involves the direct administration of a stabilized dispersion to the lung. In this regard, direct pulmonary administration of macromolecules is particularly effective in the treatment of disorders especially where poor vascular circulation of diseased portions of a lung reduces the effectiveness of intravenous drug delivery. With respect to LDI the stabilized dispersions are preferably used in conjunction with partial liquid ventilation or total liquid ventilation. Moreover, the present invention may further comprise introducing a therapeutically beneficial amount of a physiologically acceptable gas (such as nitric oxide or oxygen) into the pharmaceutical microdispersion prior to, during or following administration.

C. Methods Associated with Improved Bioavailability

In another aspect of the invention, methods for improving the local and/or systemic bioavailability of a macromolecule delivered to or via the respiratory tract are provided. Generally, the bioavailability of the macromolecule maybe improved by modifying the rate of release of the macromolecule from the lipid-based microstructure such that at least about 95% of the incorporated macromolecule is released within about 30 minutes after exposure to an aqueous environment to thereby reducing scavenging by bronchoalveolar macrophages and/or mucociliary clearance after administration to or via the respiratory tract.

Macromolecules have a natural tendency to interact or associate with the matrix of conventional microstructures, thus creating retentive structures with limited bioavailability. However, the present invention provides methods for improving the bioavailability of macromolecules that comprise incorporating the macromolecules in lipid-based microstructures such that at least about 95%, preferably 99% of the macromolecules incorporated therein are released from the lipid-based microstructures within about 30 minutes after administration to or via the respiratory tract or after exposure to an aqueous environment. In a particularly preferred embodiment, at least about 60%, preferably 80%, more preferably 90%, and most preferably 99% of the macromolecules incorporated therein are released from the lipid-based microstructures within about 15 minutes after administration to or via the respiratory tract or after exposure to an aqueous environment.

In yet another aspect of the invention, methods for administering a macromolecule with improved local and/or systemic bioavailability to or via the respiratory tract of a patient in need of treatment are provided. Such methods comprise administering a therapeutically or prophylactically effective amount of a composition comprising a plurality of the lipid-based microstructures, wherein the lipid-based microstructures are formulated so as to release about 95%, preferably 99% of the macromolecules incorporated therein within about 30 minutes after administration to the patient. Again, in a particularly preferred embodiment, at least about 60%, preferably 80%, more preferably 90%, and most preferably 99% of the macromolecule incorporated therein is released from the lipid-based microstructure within about 15 minutes after administration to the patient.

Any lipid-based microstructure described herein may be used in the disclosed methods associated with improved bioavailability. However, it has been unexpectedly discovered according to the present invention that the inclusion of at least one detergent surfactant in the lipid-based microstructure further enhances the local and/or systemic bioavailability of the incorporated macromolecule upon administration to or via the respiratory tract by reducing microstructure scavenging and/or clearance. As such, preferred lipid-based microstructures for improving local and/or systemic bioavailability of the macromolecule incorporated therein include those comprising at least one major lipid excipient, at least one minor carbohydrate excipient, and at least one minor detergent surfactant excipient.

It has also been unexpectedly discovered according to the present invention that the inclusion of a short-chain phosphatide as a major lipid excipient of the lipid-based microstructure results in even more enhanced systemic bioavailability of the incorporated macromolecule. A particularly preferred lipid-based macromolecule in this regard comprises a major lipid excipient selected from the group consisting of short-chain phosphatides having a hydrocarbon chain length of between 5 and 10 carbon atoms, a minor carbohydrate excipient, and optionally, at least one minor co-excipient selected from the group consisting of polyvalent metal ions, detergent surfactants, and combinations thereof.

The present invention will be further understood with reference to the following non-limiting examples.

EXAMPLES

Example 1

Construction of Spray Dried Metal/Lipid-Based Microstructures ("SDMLM")

The following metal ion-lipid complex based microstructure composition of this Example was manufactured by a spray dry process. An aqueous preparation was prepared by mixing a combination of preparations A and B with preparation C immediately prior to spray drying.

Preparation A was comprised of a liposome suspension of 0.57 g of DPPC dispersed in 23 g of hot DI water with a T-25 Ultraturrax at 9000 rpm for about 5 min. The coarse liposomes were homogenized under high pressure (18,000 psi) for 5 discrete passes with an Avestin Emulsiflex C5. Preparation B contained 0.15 g of $CaCl_2.2H_2O$ and 0.17 g of lactose monohydrate and 11.7 mg of TYLOXAPOL (phenol. 4-(1,1,3,3-tetramethylbutyl) polymer with formaldehyde and oxirane).

Preparation A was added to dissolve all the ingredients in preparation B, now called preparation (A+B). Preparation C contained 50.6 mg of Human IgG (Sigma Chemical Co.) dissolved in 2 mL of 0.9% NaCl. Four grams of preparation A+B was added to preparation C. The combined feed preparation was spray dried with a standard B-191 Mini spray drier equipped with a modified high efficiency cyclone under the following conditions: inlet temperature=70° C.; outlet temperature=43° C.; aspirator=84%; pump=2.2 mL/min; and, nitrogen flow=2400 L/h.

The final % weight composition of the microstructure was DPPC: $CaCl_2.2H_2O$: Lactose: hIgG: TYLOXAPOL (phenol. 4-(1,1,3,3-tetramethylbutyl) polymer with formaldehyde and oxirane)(47:12:15:25:1). The resulting powder comprised distinct, compact particles of geometric sizes in the range of 1–5 µm.

Example 2

Construction of Spray Dried Metal-Lipid Based Microstructures Co-Formulated with Surfactant-Detergent ("SDMLM-Tyl")

The following metal ion-lipid complex based microstructure composition for an improved release of the active ingredient was manufactured by a spray dry process. An aqueous preparation was prepared by mixing a combination of preparations A and B with preparation C immediately prior to spray drying.

Preparation A was comprised of a liposome suspension of 0.57 g of DPPC dispersed in 23 g of hot DI water with a T-25 Ultraturrax at 9000 rpm for about 5 min. The coarse liposomes were homogenized under high pressure (18,000 psi) for 5 discrete passes with an Avestin Emulsiflex C5. Preparation B contained 0.15 g of $CaCl_2.2H_2O$ and 0.17 g of lactose monohydrate and 11.7 mg of tyloxapol.

Preparation A was added to dissolve all the ingredients in preparation B, now called preparation (A+B). Preparation C contained 53.6 mg of Human IgG (Sigma Chemical Co.) or 0.5 mg of anti-CD3ε monoclonal antibody (PharMingen-BD) dissolved in 2 mL of 0.9% NaCl.

Four grams of preparation A+B was added to preparation C. The combined feed preparation was spray dried with a standard B-191 Mini spray drier equipped with a modified high efficiency cyclone under the following conditions: inlet temperature=70° C.; outlet temperature=43° C.; aspirator=84%; pump=2.2 mL/min; and, nitrogen flow=2400 L/h.

The final % weight composition of the microstructure was DPPC: $CaCl_2.2H_2O$: Lactose: hIgG: Tyloxapol (47:12:15: 25:1). The resulting powder comprised distinct, compact particles of geometric sizes in the range of 1–5 μm.

Example 3

Construction of Spraydried, Short-Chain, Lipid-Based Microstructures ("SDSCM")

The following metal ion-lipid complex based microstructure composition for an improved release of the active ingredient was manufactured by a spray dry process. An aqueous preparation was prepared by mixing two preparations, A and B, immediately prior to spray drying.

Preparation A was comprised of a liposome/micellar suspension of 0.14 g of dioctanoyl phosphatidylcholine, 0.04 g of $CaCl_2.2H_2O$ and 0.716 g of lactose dispersed in 23 g of hot DI water. Preparation B contained 58.6 mg of Human IgG (Sigma Chemical Co.) dissolved in 2 mL of 0.9% NaCl.

Four grams of preparation A was added to preparation B. The combined feed preparation was spray dried with a standard B-191 Mini spray drier equipped with a modified high efficiency cyclone under the following conditions: inlet temperature=60° C.; outlet temperature=38° C.; aspirator=100%; pump=2.2 mL/min; and, nitrogen flow=2400 L/h.

The final % weight composition of the microstructure was Dioctyl-PC: $CaCl_2.2H_2O$: Lactose: hIgG (12:3:60:25). The resulting powder comprised distinct, compact particles of geometric sizes in the range of 1–5 μm.

Example 4

Construction of Spray-Dried Microstructures ("SDM") Co-Formulated with Surfactant Detergent ("SDM-Tyl")

The following microstructure composition for an improved release of the active ingredient was manufactured by a spray dry process. An aqueous preparation was prepared by mixing two preparations, a combination of preparations A and B with preparation C immediately prior to spray drying.

Preparation A was comprised of a liposome suspension of 0.57 g of DPPC dispersed in 23 g of hot DI water with a T-25 Ultraturrax at 9000 rpm for about 5 min. The coarse liposomes were homogenized under high pressure (18,000 psi) for 5 discrete passes with an Avestin Emulsiflex C5.

Preparation B contained 0.17 g of lactose monohydrate and 11.7 mg of TYLOXAPOL (phenol 4-(1,1,3,3-tetramethylbutyl) polymer with formaldehyde and oxirane). As a control, lactose monohydrate only was used. Preparation A was added to dissolve all the ingredients in preparation B, now called preparation (A+B).

Preparation C contained 53.6 mg of Human IgG (Sigma Chemical Co.) or 0.5 mg of anti-CD3ε monoclonal antibody (PharMingen-BD) dissolved in 2 mL of 0.9% NaCl. Four grams of preparation A+B was then added to preparation C. The combined feed preparation was spray dried with a standard B-191 Mini spray drier equipped with a modified high efficiency cyclone under the following conditions: inlet temperature=70° C.; outlet temperature=43° C.; aspirator=84%; pump=2.2 mL/min; and, nitrogen flow=2400 L/h.

The final % weight composition of the microstructures were DPPC: Lactose: hIgG: TYLOXAPOL (phenol, 4-(1,1, 3,3-tetramethvlbutvflvolymer with formaldehyde and oxirane) Tylexapel (50:24:25:1) and DPPC: Lactose: anti-CD3ε: TYLOXAPOL (phenol, 4-(1,1,3,3-tetramethylbutyl) polymer with formaldehyde and oxirane) (50:48.5:0.5:1). The resulting powder comprised distinct, compact particles of geometric sizes in the range of 1–5 μm.

Example 5

Measurement of Total Amount of Immunoglobulin Formulated in Microstructures (SDM, SDM-Tyl, SDMLM, SDMLM-Tyl and SDSCLM)

Defined amounts of microstructures suspended in perfluorocarbon (perflubron) were dried on plastic wells and incubated for 30 minutes at 37° C. with 1 ml of normal saline (phosphate buffered saline, 1×) supplemented with 0.1% SDS under strong shaking. After incubation, the solution was harvested and centrifuged (10,000 RPM for 5 minutes) and the concentration of human IgG in supernatant was measured using a capture ELISA strategy. For this, the plates were coated with a mixture of anti-Human k+anti-Human γ light chain monoclonal antibodies (1:500+1:500 dilution; PharMingen, San Diego, Calif.), blocked with SeaBlock (Pierce) and incubated with samples for 2 hours at room temperature. The reaction was developed using the following consecutive steps: addition of 1:1000 anti-Human IgG coupled to alkaline phosphatase (Sigma) and pNPP substrate (Sigma Immunochemical). The signal was read using an automatic ELISA reader (Molecular Devices) set for 405 nm. The concentration was interpolated from a standard curve constructed with non-formulated hIgG in saline-0.1% SDS. The results (see FIG. 1) were expressed as OD measured at 405 nm corresponding to different amounts of formulated immunoglobulin, calculated based on the amount of excipients used (i.e. 25% hIgG w/w so that 1 mg of immunoglobulin corresponds to 4 mg of microstructures).

The data in FIG. 1 demonstrate that upon formulation the immunoglobulins retain the expression of light and heavy chain epitopes as well as the gross quaternary structure (complex of heavy and light chains). Secondly, based on comparison with standard curve and the amount of excipients used for formulation, the data show complete incorporation of immunoglobulins in microstructures.

Example 6

Measurement of the Amount of Immunoglobulin Released from Various Microstructures (SDM, SDM-Tyl, SDMLM, SDMLM-Tyl and SDSCLM) upon 15 Minutes Incubation with Saline 20 μg of dried microstructures corresponding to 5 μg of formulated hIgG were incubated with normal saline for 15 minutes at 37° C. under mild shaking. The suspension was centrifuged at 10,000 RPM for 5 minutes and the concentration of hIgG in supernatant was measured by capture ELISA: the read-out plates were coated with a mixture of anti-Human κ+anti-Human γ light chain monoclonal antibodies (1:500+1:500 dilution; PharMingen, San Diego, Calif.), blocked with SeaBlock (Pierce) and incubated with samples for 2 hours at room temperature. The reaction was developed using the following consecutive steps: addition of 1:1000 anti-Human IgG coupled to alkaline phosphatase (Sigma) and pNPP substrate (Sigma Immunochemical). The signal was read using an automatic ELISA reader (Molecular Devices) set for 405 nm. In order to control for the effect of co-excipients on the read-out reagents, we interpolated the results from standard curves constructed with dose-matched amounts of non-formulated hIgG added to immunoglobulin-free microstructures. The total amount of immunoglobulin in microstructures was validated using a method described in Example 5. The results were expressed as % hIgG released (and retained) for each category of microstructures (see FIG. 2). The data demonstrate that the control of fast versus slow release can be achieved by modifying the major excipient (i.e. short chain phospholipids afford increased release of hIgG at 15 minutes) or by addition of biocompatible surfactant-detergent (i.e. faster release with co-formulated tyloxapol TYLOXAPOL (phenol, 4-(1,1,3,3-tetramethylbutyl) polymer with formaldehyde and oxirane).

Example 7

Preservation of Antigen-Combining Site and Functionality of Antibodies upon Formulation in Metal-Lipid Surfactant-Detergent Microstructures ("SDMLM-Tyl")

The activity of monoclonal antibody (model anti-CD3ε. mAb, PharMingen, San Diego, Calif.) after formulation was validated using a combined capture ELISA/bioassay approach. A formulation was generated, based on metal-lipid as major excipient and TYLOXAPOL (phenol, 4-(1,1,3,3-tetramethylbutyl) polymer with formaldehyde and oxirane (1% w/w) as minor excipient, containing 0.5% monoclonal antibody. 20 μg of dried formulation was incubated with 1 ml of normal saline for 30 minutes at 37° C. under strong shaking. The suspension was clarified by centrifugation (10,000 RPM for 5 minutes) and the amount of released mAb was measured by capture ELISA as follows: the read-out plates were coated with anti-Hamster light chain monoclonal antibody (1:500 dilution; PharMingen, San Diego-Calif.), blocked with SeaBlock (Pierce) and incubated with two-fold, serial-diluted samples for 2 hours at room temperature. The reaction was developed using the following consecutive steps: addition of 1:1000 anti-Hamster IgG coupled with biotin (PharMingen), 1:1000 streptavidin-alkaline phosphatase (Sigma) and pNPP substrate (Sigma Immunochemical). The signal was read using an automatic ELISA reader (Molecular Devices) set for 405 nm. The amount of released mAb was estimated by interpolation on the linear part of a standard curve generated with non-formulated anti-CD3ε. mAb.

The bioactivity of formulated immunoglobulin was assessed by incubating various dilutions of supernatants generated as described above, with a read-out T cell hybridoma (TcH) permanently transfected with a reporter gene (β-galactosidase) controlled by the IL-2 promoter. Engagement of TCR-associated CD3ε on TcH by anti-CD3ε mAb leads to transcription of reporter gene from the IL-2 promoter. The higher the concentration of functional mAb, the higher the number of β-galactosidase$^+$ TcH. The number of activated TcH was measured after 4-hour incubation of diluted supernatant with $2\times10^4$ cells, at 37° C. and 5% $CO_2$. Briefly, the cells were washed with PBS, fixed with formaldehyde+glutaraldehyde and X-gal substrate was added for >8 hours at room temperature. The β-galactosidase$^+$ (blue) cells were counted by microscopy.

The results in FIG. 3 are represented as a two-dimensional plot of number activated TcH at various dilutions of supernatant (corresponding to different OD 405 nm values, obtained by ELISA). As a control, non-formulated anti-CD3ε mAb were used. FIG. 3 shows that the most effective route to achieve enhanced concentrations of immunoglobulins in the lung is the respiratory route (30 times more effective than the parenteral route).

Example 8

Respiratory Delivery of Immunoglobulins Formulated in Microstructures (SDM, SDM-Tyl, SDMLM, SDMLM-Tyl and SDSCLM)

BALB/c mice (females, 2-months old purchased from Taconic Farms) were anesthetized with Metofane and instilled with 40 μl saline phosphate buffer saline, 1×) or perfluorocarbon (perflubron) microstructure-hIgG suspension (SDM, SDM-Tyl, SDMLM, SDMLM-Tyl or SDSCLM, described in the EXAMPLES 1–4, suspended at 20 mg/ml in mentioned vehicle) via nostrils. At 1 hour after instillation, the mice were anesthetized again, bled by sectioning the right axillar artery and the lungs were harvested, deposited in cryogenic tubes and immersed in liquid nitrogen. The tissues were homogenized in a total volume of 1 ml of sterile saline supplemented with 10.0 g of aprotinin (Sigma). After centrifugation at 10,000 RPM for 5 minutes, the concentration of human IgG in supernatants was measured by capture ELISA. Briefly, the read-out plates were coated with a mixture of anti-Human κ+anti-Human γ light chain monoclonal antibodies (1:500+1:500 dilution; PharMingen, San Diego, Calif.), blocked with SeaBlock (Pierce) and incubated with samples for 2 hours at room temperature. The reaction was developed using the following consecutive steps: addition of 1:1000 anti-Human IgG coupled to alkaline phosphatase (Sigma) and pNPP substrate (Sigma Immunochemical). The signal was read using an automatic ELISA reader (Molecular Devices) set for 405 nm. The concentration of hIgG was interpolated on the linear part of a standard curve constructed with non-formulated immunoglobulin in PBS-10 µg/ml aprotinin. The final results were normalized to the volume of lungs (200 µl).

The results in FIG. 4A represent the concentration of hIgG in lungs (mean±SEM, n=4), one hour after the administration of non-formulated hIgG (saline) via the respiratory tract or intravenously (50 µl of solution, 2.5 mg/kg of hIgG). FIG. 4 shows that the most effective route to achieve enhanced concentrations of immunoglobulins in the lung is the respiratory route (30 times more effective than the parenteral route).

The results in FIG. 4B represent the concentration of hIgG in lungs (mean±SEM, n=4), one hour after the administration of 50 µl of suspension of microstructures in perfluorocarbon, via the respiratory tract (10 mg/kg of hIgG). As a control, the concentrations of lung hIgG were measured subsequent to intravenous administration of dose-matched immunoglobulin in saline. The results in FIG. 4B show that different species of microstructures are endowed with different efficacy of delivering hIgG to the pulmonary tissue. Highest efficacy is displayed by microstructures co-formulated with biocompatible surfactant-detergent.

Example 9

Systemic Bioavailability of Immunoglobulins Formulated in Microstructures (SDM, SDM-Tyl, SDMLM, SDMLM-Tyl and SDSCLM) upon Administration to the Respiratory Tract BALB/c mice (females, 2-months old purchased from Taconic Farms) were anesthetized with Metofane and instilled with perfluorocarbon-microstructure-hIgG suspension (described in the EXAMPLES 1–4, suspended at 20 mg/ml in mentioned vehicle) via nostrils (10 mg/kg of formulated hIgG). Dose-matched hIgG in saline was administered intravenously into control mice. At 1 hour and 3 days after instillation or injection, sera were harvested from the mice and the concentration of hIgG was measured by capture ELISA. Briefly, the read-out plates were coated with a mixture of anti-Human k+anti-Human γ light chain monoclonal antibodies (1:500+1:500 dilution; PharMingen, San Diego, Calif.), blocked with SeaBlock (Pierce) and incubated with samples for 2 hours at room temperature. The reaction was developed using the following consecutive steps: addition of 1:1000 anti-Human IgG coupled to alkaline phosphatase (Sigma) and pNPP substrate (Sigma Immunochemical). The signal was read using an automatic ELISA reader (Molecular Devices) set for 405 nm. The concentration of hIgG was interpolated on the linear part of a standard curve constructed with non-formulated immunoglobulin in mouse serum (Sigma Immunochemical).

The results are expressed in FIG. 5 as means±SEM (n=4) of serum concentrations corresponding to different experimental groups. FIG. 5 shows that various species of particles have different efficacy in delivering systemically hIgG upon administration to the respiratory tract. The highest efficacy is provided by microstructures based on short-chained phospholipids (SDSCLM) or co-formulated with surfactant-detergent (SDM-Tyl; SDMLM-Tyl.)

Example 10

Local Delivery of Immunoglobulin, by Aerosolization of SDMLM or SDMLM-Tyl into the Airways Sprague Dawley rats were anesthetized with isoflurane and treated with aerosols generated using a device (Penn-Century insufflator®) inserted into the trachea. The device was loaded with 20 mg/ml suspension of particles in perflubron. One dose corresponded to 40 µl of suspension, containing 800 µg of formulation with 200 µg of immunoglobulin. SDMLM formulation was used, with or without 1% TYLOXAPOL (phenol, 4-(1,1,3,3-tetramethylbutyl) polymer with formaldehyde and oxirane). As controls, we used rats injected i.v. with a dose-matched amount of hIgG in saline.

One hour after administration, lung tissues were harvested and homogenized in sterile saline supplemented with 10 µg of aprotinin (Sigma). After centrifugation at 10,000 RPM for 5 minutes, the concentration of human IgG in supernatants was measured by capture ELISA. Briefly, the read-out plates were coated with a mixture of anti-Human k+anti-Human γ light chain monoclonal antibodies (1:500+1:500 dilution; PharMingen, San Diego, Calif.), blocked with SeaBlock (Pierce) and incubated with samples for 2 hours at room temperature. The reaction was developed using the following consecutive steps: addition of 1:1000 anti-Human IgG conjugated to alkaline phosphatase (Sigma) and developed with pNPP substrate (Sigma Immunochemical). The signal was read at 405 nm using a microtiterplate reader (Molecular Devices). The concentration of hIgG was interpolated on the linear part of a standard curve constructed with non-formulated immunoglobulin in PBS-10 µg/ml aprotinin. The final results were normalized to the volume of lungs (1.8 ml).

The data are represented as mean ±SEM of total amount of immunoglobulin recovered in the lungs of treated rats. They show that addition of TYLOXAPOL (phenol, 4-(1,1, 3,3-tetramethylbutyl) polymer with formaldehyde and oxirane) greatly improved the local pulmonary retention and bioavailability upon aerosolization of the SDMLM particle formulation.

While the present invention has been particularly shown and described with reference to the examples and preferred embodiments described herein, it will be understood by those skilled in the art that various changes in form and details may be made without departing from the scope of the invention encompassed by the appended claims.

What is claimed:

1. A method for improving the local and/or systemic bioavailability of a macromolecule upon administration to or via the respiratory tract of a patient in need of treatment, the method comprising:
   incorporating said macromolecule into a lipid-based microstructure that comprises:
   (a) a major lipid excipient comprising a major amount of the lipid-based microstructure based on the total weight of the microstructure, the major lipid excipient comprising a lipid excipient or a mixture of lipid excipients; and
   (b) a minor co-excipient comprising a minor amount of the lipid-based microstructure based on the total weight of the microstructure, the minor amount being lesser than the major amount, and the minor co-excipient being selected from the group consisting of detergent surfactants, carbohydrates, and combinations thereof;

wherein said lipid-based microstructure is formulated so as to release at least about 95% of said macromolecule incorporated therein within about 30 minutes after administration to or via the respiratory tract of said patient in need of treatment to thereby at least partially avoid scavenging by bronchoalveolar macrophages and/or a mucociliary clearance after said administration and improve said local and/or systemic bioavailability of said macromolecule.

2. The method of claim 1, wherein said lipid-based microstructure is formulated so as to release at least about 99% of said macromolecule incorporated therein within about 30 minutes after said administration.

3. The method of claim 1, wherein said lipid-based microstructure is formulated so as to release at least about 80% of said macromolecule incorporated therein within about 15 minutes after said administration.

4. The method of claim 1, wherein said lipid-based microstructure is formulated so as to release at least about 80% of said macromolecule incorporated therein within about 15 minutes after said administration.

5. The method of claim 1, wherein said lipid-based microstructure is formulated so as to release at least about 90% of said macromolecule incorporated therein within about 15 minutes after said administration.

6. The method of claim 1, wherein said lipid-based microstructure is formulated so as to release at least about 99% of said macromolecule incorporated therein within about 15 minutes after said administration.

7. The method of claim 1, wherein said major lipid excipient is present in said lipid-based microstructure in an amount ranging from about 10% to about 89% w/w.

8. The method of claim 1, wherein said major lipid excipient is present in said lipid-based microstructure in an amount ranging from about 25% to about 75% w/w.

9. The method of claim 1, wherein said major lipid excipient comprises a phosphatide.

10. The method of claim 9, wherein said phosphatide is selected from the group consisting of homo and heterochain phosphatidylcholines, phosphatidylserines, phosphatidylethanolamines, phosphatidyiglycerols, phosphatidylinositols, sphingomyelins, gangliosides, 3-trimethylammonium-propane phosphatides and dimethylammonium-propane phosphatides, having a hydrocarbon chain length ranging from 5 to 22 carbon atoms.

11. The method of claim 9, wherein said phosphatide is hydrogenated, unsaturated or partially hydrogenated.

12. The method of claim 9, wherein said phosphatide is selected from the group consisting of dipalmitoleioylphosphatidylcholine (DiC8PC), distearoylphosphatidylcholine (DiC16PC), dipalmitoylphosphatidylcholine (DiC14PC), dicaproylphosphatidylcholine (DiC8PC), dioctanoylphosphatidylcholine (DiC6PC), distearoylphosphatidylserine (DiC16PS), dipalmitoylphosphatidylserine (DIC14PS), dicaproylphosphatidylserine (DiC8PS), dioctanoylphosphatidylserine (DiC6PS), and combinations thereof.

13. The method of claim 9, wherein said phosphatide is selected from the group consisting of dipalmitoylphosphatidylcholine, dioctanoyl phosphatidylcholine, and combinations thereof.

14. The method of claim 9, wherein said phosphatide is a short-chain phosphatide selected from the group consisting of homo and heterochain phosphatidylcholines, phosphatidylserines, phosphatidylethanolamines phosphatidyiglycerols, phosphatidylinositols, sphingomyelins, gangliosides, 3-trimethylammonium-propane phosphatides and dimethylammonium-propane phosphatides, having a hydrocarbon chain length ranging from 5 to 10 carbon atoms.

15. The method of claim 14, wherein said phosphatide is selected from the group consisting of dicaproylphosphatidylcholine (DiC8PC), dioctanoylphosphatidylcholine (DiC6PC), dicaproylphosphatidylserine (DiC8PS), dioctanoylphosphatidylserine (DiC6PS), and combinations thereof.

16. The method of claim 15, wherein said phosphatide is dioctanoyl phosphatidylcholine.

17. The method of claim 1, wherein said minor co-excipient comprises a carbohydrate excipient present in said lipid-based microstructure in an amount ranging from about 1% to about 70% w/w.

18. The method of claim 17, wherein said carbohydrate excipient is present in said lipid-based microstructure in an amount ranging from about 5% to about 50% w/w.

19. The method of claim 17, wherein said carbohydrate excipient is selected from the group consisting of: hetastarch, starches, lactose, mannitol, mannose, inulin, mannan, sorbitol, galactitol, sucrose, trehalose, raffinose, maltose, glucose, cellulose and derivatives, pectins, dextrans, dextrins, chitosan, chitin, mucopolysaccharides, chondroitin sulfate, and saponins.

20. The method of claim 1, wherein said minor co-excipient comprises a detergent surfactant excipient present in said lipid-based microstructure in an amount of about 10% w/w or less.

21. The method of claim 20, wherein said detergent surfactant excipient is present in said lipid-based microstructure in an amount ranging from about 0.5% to about 5% w/w.

22. The method of claim 20, wherein said detergent surfactant excipient is selected from the group consisting of POLOXAMER's (polyethylene-polypropylene glycol, which is a nonionic it polyoxyethylene-polyoxypropylene block co-polymer), TWEEN's (polyoxyethylene sorbitan monolaurate), TRITON's (2,4,6-Trinitrotoluene), polyethylene glycols, and sugar esters.

23. The method of claim 22, wherein said detergent surfactant excipient is selected from the group consisting of POLOXAMER 188 (polyethylene-polypropylene glycol with an average molecular weight of 8400 g/mol). POLOXAMER 407 (polyethylene-polypropylene glycol with an average molecular weight of 12.500 g/mol), TWEEN 80 (polyoxyethylene sorbitan monooleate), PEG 1540 (Polyethylene gycols with an average molecular weight of 1500 g/mol), cetyl alcohol, and TYLOXAPOL (phenol, 4-(1,1,3, 3-tetramethylbutyl) polymer with formaldehyde and oxirane).

24. The method of claim 1, wherein said lipid-based microstructure further comprises a polyvalent metal ion.

25. The method of claim 24, wherein said polyvalent metal ion is present in said lipid-based microstructure in a metal/lipid molar ratio of about 2 or less.

26. The method of claim 24, wherein said polyvalent metal ion is selected from the group consisting of calcium, magnesium, aluminum and zinc.

27. The method of claim 1, wherein said macromolecule is selected from the group consisting of: peptides, proteins, nucleotides, and immunogenic agents.

28. The method of claim 1, wherein said macromolecule is a protein antigen.

29. The method of claim 28, wherein said protein antigen is an immunoglobulin or an immunoglobulin-like molecule.

30. The method of claim 1, wherein said lipid-based microstructures are dispersed in a nonaqueous suspension medium.

31. The method of claim 30, wherein said nonaqueous suspension medium comprises a compound selected from the group consisting of hydrofluoroalkanes, fluorocarbons, perfluorocarbons, fluorocarbon/hydrocarbon diblocks, hydrocarbons, alcohols, ethers, and combinations thereof.

32. The method of claim 30, wherein said nonaqueous suspension medium comprises a compound selected from the group consisting of liquid fluorochemicals and hydrofluoroalkane propellants.

33. The method of claim 1, wherein the mean aerodynamic diameter of said lipid-based microstructure is between 0.5 and 5 µm.

34. The method of claim 1, wherein the mean geometric diameter of said lipid-based microstructure ranges from about 1 to about 30 µm.

35. The method of claim 1, wherein said lipid-based microstructure has a bulk density ranging from about 0.1 to about 0.5 g/cm$^3$.

36. The method of claim 1, wherein said lipid-based microstructure has a structural matrix selected from the group consisting of particulates, microparticulates, perforated microstructures, and combinations thereof.

37. The method of claim 1, wherein said lipid-based microstructure is a perforated microstructure.

38. The method of claim 1, wherein said lipid-based microstructure is formulated so as to be capable of administration to or via the respiratory tract of said patient in need of treatment using a delivery methodology selected from the group consisting of liquid dose instillation, nebulization, aerosolization, dry powder inhalation, and metered dose inhalation.

39. The method of claim 1, wherein said microstructure comprises a miner detergent surfactant excipient present in said lipid-based microstructure in an amount of about 10% w/w or less, and a carbohydrate excipient present in said lipid-based microstructure in an amount ranging from about 1% to about 70% w/w.

* * * * *